(12) United States Patent
Jang et al.

(10) Patent No.: US 9,522,879 B2
(45) Date of Patent: Dec. 20, 2016

(54) METHOD FOR PREPARING POLYTHIOL COMPOUND AND POLYMERIC COMPOSITION FOR OPTICAL MATERIAL COMPRISING SAME

(71) Applicant: KOC SOLUTION CO., LTD, Daejeon (KR)

(72) Inventors: Dong Gyu Jang, Daejeon (KR); Soo Gyun Roh, Daejeon (KR); Jong Hyo Kim, Daejeon (KR)

(73) Assignee: KOC SOLUTION CO., LTD, Yuseong-Gu Daejeon (KR)

( * ) Notice: Subject to any disclaimer, the term of this patent is extended or adjusted under 35 U.S.C. 154(b) by 64 days.

(21) Appl. No.: 14/402,573

(22) PCT Filed: May 23, 2013

(86) PCT No.: PCT/KR2013/004541
§ 371 (c)(1),
(2) Date: Nov. 20, 2014

(87) PCT Pub. No.: WO2013/176506
PCT Pub. Date: Nov. 28, 2013

(65) Prior Publication Data
US 2015/0148512 A1    May 28, 2015

(30) Foreign Application Priority Data

May 23, 2012  (KR) ........................ 10-2012-0054761
Jun. 29, 2012  (KR) ........................ 10-2012-0071101

(51) Int. Cl.
| | | |
|---|---|---|
| C07C 319/20 | (2006.01) |
| C07C 301/02 | (2006.01) |
| C08G 18/38 | (2006.01) |
| G02B 1/04 | (2006.01) |
| C07C 319/14 | (2006.01) |
| C07C 319/08 | (2006.01) |
| C07C 321/14 | (2006.01) |
| C07C 323/12 | (2006.01) |
| C08L 81/00 | (2006.01) |
| C07C 321/08 | (2006.01) |
| C07D 301/02 | (2006.01) |
| C08G 18/75 | (2006.01) |
| C08G 18/76 | (2006.01) |

(52) U.S. Cl.
CPC ........... C07C 319/20 (2013.01); C07C 319/08 (2013.01); C07C 319/14 (2013.01); C07C 321/08 (2013.01); C07C 323/12 (2013.01); C07D 301/02 (2013.01); C08G 18/3868 (2013.01); C08G 18/3876 (2013.01); C08G 18/755 (2013.01); C08G 18/7671 (2013.01); C08G 18/7692 (2013.01); G02B 1/041 (2013.01); G02B 1/043 (2013.01)

(58) Field of Classification Search
CPC .... C07C 319/20; C07C 319/14; C07C 319/08; C07C 321/14; C07C 323/12; C08G 18/3876; C08G 18/3868; G02B 1/041; G02B 1/043; C08L 81/00
See application file for complete search history.

(56) References Cited

U.S. PATENT DOCUMENTS 5,837,797 A * 11/1998 Okazaki ............... C07C 321/14
264/1.1

FOREIGN PATENT DOCUMENTS

| JP | 09-0194558 | 7/1997 |
|---|---|---|
| JP | 9-194588 A * | 7/1997 |
| KR | 10-1995-0001404 | 5/1999 |
| KR | 10-2004-0060966 | 2/2007 |
| KR | 10-2008-0086993 | 9/2008 |
| KR | 10-2011-0021371 | 3/2011 |

* cited by examiner

*Primary Examiner* — Rabon Sergent
(74) *Attorney, Agent, or Firm* — Susan Paik, Esq.

(57) ABSTRACT

The present invention relates to novel methods for preparing a polythiol compound for use in an optical material and polymerizable compositions including a polythiol compound prepared by the methods. According to the methods, a polythiol compound with uniform color, high purity and high quality can be prepared at reduced cost. The polymerizable compositions can be used to manufacture clear, transparent optical lenses with good heat resistance and excellent optical properties.

12 Claims, No Drawings

METHOD FOR PREPARING POLYTHIOL COMPOUND AND POLYMERIC COMPOSITION FOR OPTICAL MATERIAL COMPRISING SAME

TECHNICAL FIELD

The present invention relates to novel methods for preparing a polythiol compound for use in an optical material and polymerizable compositions including a polythiol compound prepared by the methods. More particularly, the present invention relates to methods for preparing a polythiol compound with uniform color, high purity and high quality at reduced cost, and polymerizable compositions including a polythiol compound prepared by the methods that can be used to manufacture clear, transparent optical lenses with good heat resistance and excellent optical properties.

BACKGROUND ART

Plastic optical materials are more lightweight, less brittle, and more easily dyeable than optical materials composed of inorganic materials. Numerous plastic resin materials have been applied to optical materials and have been increasingly required to have excellent physical properties.

Polythiourethane optical resins produced using polythiol compounds and isocyanate compounds are widely used as materials for optical lenses due to their excellent optical properties in terms of transparency, Abbe number, and transmittance, and physical properties in terms of tensile strength.

Korean Patent Application No. 10-1995-001404 discloses a method for preparing a polythiol compound. According to this method, epichlorohydrin is reacted with 2-mercaptoethanol in the presence of triethylamine to obtain a diol, and the diol is reacted with sodium sulfide to obtain a tetraol. The tetraol is reacted with thiourea in hydrochloric acid to prepare an isothiouronium salt. Subsequently, rearrangement takes place to form a tetraisothiouronium salt. The tetraisothiouronium salt is hydrolyzed by the addition of aqueous ammonia to obtain the desired polythiol compound.

The patent application discloses another method for preparing a polythiol compound. According to this method, epichlorohydrin is reacted with thioglycerol in the presence of triethylamine to obtain a triol. Then, the reaction liquid is reacted with thionyl chloride to obtain a chlorinated derivative. At this moment, rearrangement takes place partially to form an isomer mixture tetrachloride. Then, the isomer mixture tetrachloride is reacted with thiourea to form an isothiouronium salt, to which hydrazine hydrate is added to hydrolyze the salt to obtain the desired polythiol.

Despite the advantages of simple reaction routes and low costs, the conventional methods generate large quantities of by-products and cause non-uniform colors of polythiol compounds. The by-products deteriorate the heat resistance of optical lenses, limiting the application of the polythiol compounds to resins for optical lenses.

SUMMARY OF THE INVENTION

Technical Problem

The present invention has been made in an effort to solve the above problems, and it is an object of the present invention to provide methods for preparing a polythiol compound from epichlorohydrin as a starting material via reaction schemes described herein. It is a more specific object of the present invention to provide methods for preparing a polythiol compound with uniform color and high purity at reduced cost. It is another object of the present invention to provide polymerizable compositions for optical materials including a polythiol compound prepared by the methods and optical materials (such as optical lenses) produced by polymerization of the polymerizable compositions. It is a more specific object of the present invention to provide clear, transparent optical lenses with good heat resistance and excellent optical properties.

Technical Solution

The present invention provides a method for preparing a polythiol compound from epichlorohydrin as a starting material, the method including:
reacting epichlorohydrin with hydrogen sulfide to obtain bis(3-chloro-2-hydroxypropyl)sulfide;
reacting a 2-mercaptoethanol salt with the bis(3-chloro-2-hydroxypropyl)sulfide to obtain a polyol compound;
adding hydrochloric acid and thiourea to the polyol compound, stirring the mixture under heating, cooling the reaction mixture to room temperature, and adding a basic aqueous solution to the reaction mixture to hydrolyze the reaction product; and
washing the hydrolysis product with water at room temperature, followed by concentration under reduced pressure.

The present invention also provides a method for preparing a polythiol compound from epichlorohydrin as a starting material, the method including:
reacting epichlorohydrin with hydrogen sulfide in the presence of a catalyst to obtain bis(3-chloro-2-hydroxypropyl)sulfide;
adding an aqueous solution of sodium hydroxide to the bis(3-chloro-2-hydroxypropyl)sulfide to obtain an epoxy compound,
adding 2-mercaptoethanol and a catalyst to the epoxy compound to obtain a polyol compound,
adding hydrochloric acid and thiourea to the polyol compound, stirring the mixture under heating, cooling the reaction mixture to room temperature, and adding a basic aqueous solution to the reaction mixture to hydrolyze the reaction product; and
washing the hydrolysis product with water at room temperature, followed by concentration under reduced pressure.

The present invention also provides polymerizable compositions for optical materials including a polythiol compound prepared by the methods.

The present invention also provides optical materials produced by polymerization of the polymerizable compositions and optical lenses composed of the optical materials. Particularly, the optical lenses include spectacle lenses.

DETAILED DESCRIPTION

Advantageous Effects

According to the methods of the present invention, a polythiol compound with uniform color and high purity can be prepared at reduced cost. In addition, an optical lens manufactured using a polymerizable composition including the polythiol compound is clear and transparent and exhibits good heat resistance and excellent optical properties.

BEST MODE

The present invention provides a method for preparing a polythiol compound, including the steps depicted in Reaction Scheme 1.

[Reaction Scheme 1]

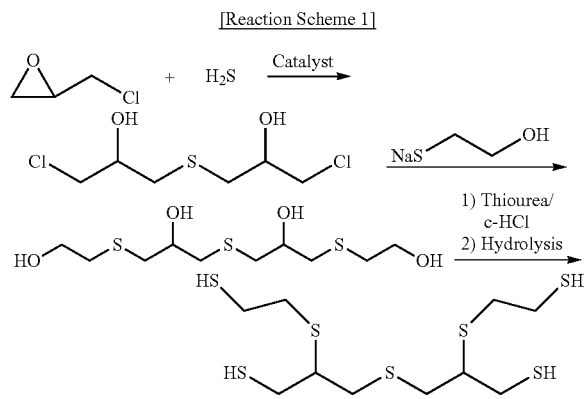

According to Reaction Scheme 1, methanol is added to epichlorohydrin, hydrogen sulfide generated from NaSH.xH$_2$O (70% NaSH) and hydrochloric acid is slowly added dropwise to the epichlorohydrin solution to form 3-chloro-2-hydroxypropanethiol, which is subsequently converted to bis(3-chloro-2-hydroxypropyl)sulfide. A 2-mercaptoethanol salt solution is added dropwise to the bis(3-chloro-2-hydroxypropyl)sulfide. The salt solution is prepared by mixing sodium hydroxide and 2-mercaptoethanol. The mixture is allowed to react for a sufficient time to obtain the polyol compound. The reaction solution is cooled to a temperature of about 20° C. with stirring, and 35% hydrochloric acid and thiourea are added thereto. The mixture is heated at about 110° C. for 3 to 10 hours. After the reaction mixture is cooled to room temperature, toluene and a basic aqueous solution are slowly added to hydrolyze the reaction product. The basic aqueous solution may be, for example, aqueous ammonia or a NaOH solution.

The obtained organic layer is cooled to room temperature, washed, and concentrated under reduced pressure to obtain the final polythiol compound, which is colorless and transparent.

The present invention also provides a method for preparing a polythiol compound, including the steps depicted in Reaction Scheme 2.

[Reaction Scheme 2]

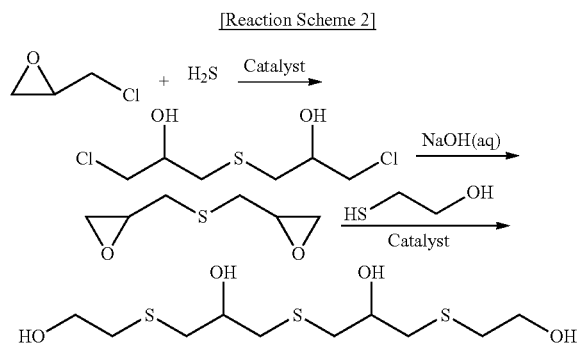

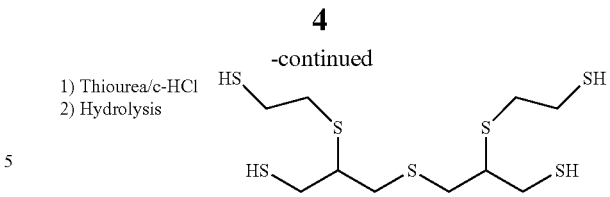

According to Reaction Scheme 2, methanol is added to epichlorohydrin, hydrogen sulfide generated from NaSH.xH$_2$O (70% NaSH) and hydrochloric acid is slowly added dropwise to the epichlorohydrin solution to form 3-chloro-2-hydroxypropanethiol, which is subsequently converted to bis(3-chloro-2-hydroxypropyl)sulfide. An aqueous solution of sodium hydroxide (NaOH) is slowly added dropwise to the bis(3-chloro-2-hydroxypropyl)sulfide to obtain an epoxy compound. 2-Mercaptoethanol is slowly added dropwise to the epoxy compound. The mixture is allowed to react for a sufficient time to obtain the polyol compound. The reaction solution is cooled to a temperature of about 20° C. with stirring, and 35% hydrochloric acid and thiourea are added thereto. The mixture is heated at about 110° C. for 3 to 10 hours. After the reaction mixture is cooled to room temperature, toluene and a basic aqueous solution are slowly added to hydrolyze the reaction product. The basic aqueous solution may be, for example, aqueous ammonia or a NaOH solution. The obtained organic layer is cooled to room temperature, washed, and concentrated under reduced pressure to obtain the final polythiol compound, which is colorless and transparent.

The present invention also provides a polymerizable composition for an optical material including the polythiol compound prepared by each of the methods. The polymerizable composition of the present invention may further include a polyisocyanate compound. Any polyisocyanate compound having at least one isocyanate group and/or at least one isothiocyanate group may be used without particular limitation. Examples of such polyisocyanate compounds include: aliphatic isocyanate compounds, such as 2,2-dimethylpentane diisocyanate, 2,2,4-trimethylhexane diisocyanate, butene diisocyanate, 1,3-butadiene-1,4-diisocyanate, 1,5-pentamethylene diisocyanate, 1,6-hexamethylene diisocyanate (HDI), 1,3,5-tris(6-isocyanatohexyl)-[1,3,5]-triazinane-2,4,6-trione (HDI trimer), 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, and bis(isocyanatoethyl)ether; alicyclic isocyanate compounds, such as isophorone diisocyanate (IPDI), dicyclohexylmethane-4,4-isocyanate (H$_{12}$MDI), bis(isocyanatomethyl)cyclohexane, o,m,p-xylene diisocyanate, α,α,α',α'-tetramethylxylylene diisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyldimethylmethane isocyanate, and 2,2-dimethyldicyclohexylmethane isocyanate; aromatic isocyanate compounds, such as tolylene diisocyanate (TDI), bis(isocyanatoethyl)benzene, bis(isocyanatopropyl)benzene, bis(isocyanatobutyl)benzene, bis(isocyanatomethyl)naphthalene, bis(isocyanatomethyl)diphenyl ether, phenylene diisocyanate, ethylphenylene diisocyanate, isopropylphenylene diisocyanate, dimethylphenylene diisocyanate, diethylphenylene diisocyanate, di isopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene di isocyanate, and hexahydrodiphenylmethane-4,4-diisocyanate; sulfur-containing aliphatic isocyanate compounds, such as bis(isocyanatoethyl)sulfide, bis(isocyanatopropyl)sulfide, bis(isocyanatohexyl)sulfide, bis(isocyanatomethyl)sulfide, bis(isocyanatomethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, and 1,5-diisocyanato-2-isocyanatomethyl-3-thiapentane; sulfur-containing aromatic isocyanate compounds, such as diphenylsulfide-2,4-diisocyanate, diphenylsulfide-4,4-diisocyanate, 3,3-dimethoxy-4,4-diisocyanatodibenzyl thioether, bis(4-isocyanatomethylbenzene)sulfide, 4,4-methoxybenzenethioethylene glycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxydiphenyldisulfide-4,4-diisocyanate, and 4,4-dimethoxydiphenyldisulfide-3,3-diisocyanate; sulfur-containing heterocyclic isocyanate compounds, such as 2,5-diisocyanatothiophene, 2,5-bis(isocyanatomethyl)thiophene, 2,5-diisocyanatotetrahydrothiophene, 2,5-bis(isocyanatomethyptetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane; and other isocyanate compounds, such as 3,8-bis(isocyanatomethyl)tricyclo[5,2,1,02,06]decane, 3,9-bis(isocyanatomethyl) tricyclo[5,2,1,02,06]decane, 4,8-bis(isocyanatomethyl) tricyclo[5,2,1,02,06]decane, 2,5-bis(isocyanatomethyl) bicyclo[2,2,1]heptane, and 2,6-bis(isocyanatomethyl) bicyclo[2,2,1]heptane. These polyisocyanate compounds may be used alone or as a mixture of two or more thereof. As the polyisocyanate compound, there may also be used, for example: a halogenated product of the polyisocyanate compound, such as a chlorinated or brominated product of the polyisocyanate compound; an alkylated product of the polyisocyanate compound; a nitro-substituted product of the polyisocyanate compound; a prepolymer modified product of the polyisocyanate compound with a polyhydric alcohol or thiol; a carbodiimide, urea or biuret modified product of the polyisocyanate compound; or a dimerization or trimerization reaction product of the polyisocyanate compound.

The polymerizable composition of the present invention may further include another polythiol compound in addition to the polythiol compound prepared by each of the methods. The additional polythiol compound is not particularly limited so long as it has at least one thiol group. Examples of such polythiol compounds include bis(2-mercaptoethyl)sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, 2-(2-mercaptoethylthio)-3-2-mercapto-3-[3-mercapto-2-(2-mercaptoethylthio)-propylthio]propylthiopropane-1-thiol, 2,2-bis(3-mercaptopropionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), tri methylolpropane tris(3-mercaptopropionate), pentaerythritol tetrakis(2-mercaptoacetate), bipentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, and 2-(2,2-bis(mercaptodimethylthio)ethyl)-1,3-dithietane. These polythiol compounds may be used alone or as a mixture of two or more thereof. As the additional polythiol compound, there may also be used, for example, a polymerization modified product obtained by prepolymerization with an isocyanate compound, a thioepoxy compound, a thietane compound, or a compound having an unsaturated bond as a resin modifier.

The polymerizable composition of the present invention may include an internal release agent. An acidic phosphate compound is preferred as the internal release agent. If needed, the polymerizable composition of the present invention may further include at least one component selected from catalysts, UV absorbers, dyes, stabilizers, and blowing agents. The polymerizable composition of the present invention may further include a compound copolymerizable with a urethane polymerizable composition. Examples of such copolymerizable compounds include epoxy compounds, thioepoxy compounds, compounds having a vinyl or unsaturated group, and metal compounds.

The present invention also provides optical materials produced by polymerization of the polymerizable compositions. Particularly, the optical materials of the present invention can be used to manufacture optical lenses. Particularly, the optical lenses include spectacle lenses. The optical lenses of the present invention may be manufactured by casting polymerization of the polymerizable compositions. Specifically, the optical lenses are manufactured by the following procedure. First, various additives and a catalyst are dissolved in the isocyanate compound. To the solution is added the polythiol compound. The mixture is degassed under reduced pressure during cooling. After the passage of a predetermined time, the degassed mixture is filled in a glass mold molded with a tape and is then cured by slow heating to a higher temperature over about 24 to about 48 hours.

The urethane optical materials of the present invention have the advantages of high refractive index, low dispersity, good heat resistance, superior durability, light weight, and good impact resistance. Particularly, the urethane optical materials of the present invention are clear and transparent due to their good color. Due to these advantages, the urethane optical materials of the present invention are suitable for use in optical products such as lenses and prisms, particularly lenses such as spectacle lenses and camera lenses.

If needed, the optical lenses of the present invention may be subjected to a physical or chemical treatment, for example, surface polishing, antistatic finishing, hard coating, antireflective coating, dyeing or dimming, for the purpose of improving antireflection, hardness, wear resistance, chemical resistance, antifog properties or fashionability.

EXAMPLES

The present invention will be explained in more detail with reference to the following examples. However, these examples are provided for illustrative purposes only and are not intended to limit the scope of the present invention.

Evaluation Methods

Refractive indices and Abbe numbers were measured using Abbe refractometers IT and DR-M4 (Atago Co., Ltd.) at 20° C.

APHA colors of polythiourethane plastic lenses were measured using a spectrophotometer (ColorQuest XE, Hunterlab). Specifically, after placing in the instrument, the APHA color of each lens was measured by comparison of a program containing data on the concentrations of reference solutions of platinum and cobalt reagents with the sample solution. The smaller the measured value, the better is the color.

Synthesis Example 1

BMPS-1 (Bis(2-(2-mercaptoethylthio)-3-mercaptopropyl)sulfide-1)

500 g (5.4 mol) of epichlorohydrin, 250 g of methanol, and 1 g of 50% NaOH (aq) were placed in a reactor. The temperature of the reactor was adjusted to 6° C. $H_2S$ generated from NaSH.$xH_2O$ (70% NaSH, 216.1 g, 2.7 mol) and 35% hydrochloric acid (281 g, 2.7 mol) was slowly added dropwise to the epichlorohydrin solution to form 3-chloro-2-hydroxypropanethiol, which was subsequently converted to bis(3-chloro-2-hydroxypropyl)sulfide (592.1 g, 5.4 mol). To 219.13 g (1.0 mol) of the bis(3-chloro-2-hydroxy-propyl)sulfide, a solution of a 2-mercaptoethanol salt, which was prepared by mixing 160 g (2.0 mol) of 50% NaOH (aq) and 156.2 g (2.0 mol) of 2-mercaptoethanol, was slowly added dropwise at 35° C. The mixture was left standing at 35° C. for 1 h to allow for sufficient reaction. As a result of the reaction, a polyol compound was obtained. The solution containing the polyol compound was cooled to 20° C. with stirring, and 624.9 g (6.0 mol) of 35% hydrochloric acid and 380.6 g (5.0 mol) of thiourea were added thereto. The mixture was heated at 110° C. for 1 h 30 min with stirring. After cooling to room temperature, 800 mL of toluene was added and then 613.0 g (9.0 mol) of 25% aqueous ammonia was slowly added. Hydrolysis of the reaction product was allowed to proceed at 65° C. for 3 h. The obtained organic layer was cooled to room temperature and washed sequentially with 200 mL of 36% hydrochloric acid, 200 mL of water, 200 mL of dilute aqueous ammonia, and 200 mL of water. The washing procedure was repeated three times. The organic layer was separated and concentrated under reduced pressure, affording the desired polythiol compound (355.76 g, 97%), which was colorless and transparent.

Synthesis Example 2

BMPS-2 (Bis(2-(2-mercaptoethylthio)-3-mercaptopropyl)sulfide-2)

500 g (5.4 mol) of epichlorohydrin, 250 g of methanol, and 1 g of 50% NaOH (aq) were placed in a reactor. The temperature of the reactor was adjusted to 6° C. $H_2S$ generated from NaSH.$xH_2O$ (70% NaSH, 216.1 g, 2.7 mol) and 35% hydrochloric acid (281 g, 2.7 mol) was slowly added dropwise to the epichlorohydrin solution to form 3-chloro-2-hydroxypropanethiol, which was subsequently converted to bis(3-chloro-2-hydroxypropyl)sulfide (592.1 g, 5.4 mol). To 219.13 g (1.0 mol) of the bis(3-chloro-2-hydroxy-propyl)sulfide, 160 g (2.0 mol) of 50% NaOH (aq) was slowly added dropwise at 15° C. The mixture was left standing for 1 h to allow for sufficient reaction. As a result of the reaction, a polyol compound was obtained. The solution containing the polyol compound was cooled to 20° C. with stirring, and 624.9 g (6.0 mol) of 35% hydrochloric acid and 380.6 g (5.0 mol) of thiourea were added thereto. The mixture was heated at 110° C. for 1 h 30 min with stirring. After cooling to room temperature, 800 mL of toluene was added and then 613.0 g (9.0 mol) of 25% aqueous ammonia was slowly added. Hydrolysis of the reaction product was allowed to proceed at 65° C. for 3 h. The obtained organic layer was cooled to room temperature and washed sequentially with 200 mL of 36% hydrochloric acid, 200 mL of water, 200 mL of dilute aqueous ammonia, and 200 mL of water. The washing procedure was repeated three times. The organic layer was separated and concentrated under reduced pressure, affording the desired polythiol compound (357.57 g, 97.5%), which was colorless and transparent.

Comparative Synthesis Example 1

BMPS-3 (Bis(2-(2-mercaptoethylthio)-3-mercaptopropyl)sulfide-3)

92.5 g (1.0 mol) of epichlorohydrin was added dropwise to a mixture of 78.1 g (1.0 mol) of 2-mercaptoethanol and 1.0 g of triethylamine over 1 h while maintaining the temperature at 35-45° C. The resulting mixture was left standing at 40° C. for 1 h. To the reaction solution was added dropwise an aqueous solution of 120.09 g (0.5 mol) of $Na_2S.9H_2O$ in 100 g of pure water over 1 h while maintaining the temperature at 40-45° C. After standing at 45° C. for 1 h, 303.8 g (3.0 mol) of 36% hydrochloric acid and 190.3 g (2.5 mol) of thiourea were added. The mixture was heated at 110° C. for 9 h with stirring. After cooling to room temperature, 400 mL of toluene was added and then 306.5 g (4.5 mol) of 25% aqueous ammonia was slowly added. Hydrolysis of the reaction product was allowed to proceed at 65° C. for 3 h. The obtained organic layer was cooled to room temperature and washed sequentially with 100 mL of 36% hydrochloric acid, 100 mL of water, 100 mL of dilute aqueous ammonia, and 100 mL of water. The washing procedure was repeated three times. The organic layer was separated and concentrated under reduced pressure, affording the desired polythiol compound (174.20 g, 95%), which was yellow in color.

Examples 1-4 and Comparative Examples 1-2

As shown in Table 1, the polythiol compound prepared in Synthesis Examples 1-2 and Comparative Synthesis Example 1, the polyisocyanate compounds, and the additives were mixed to prepare optical resin compositions. The optical resin compositions were cast polymerized to manufacture urethane optical lenses. The refractive indices, Abbe numbers, and APHA colors of the urethane optical lenses were evaluated.

TABLE 1

| | | Example No. | | | | Comparative Example No. | |
|---|---|---|---|---|---|---|---|
| | | 1 | 2 | 3 | 4 | 1 | 2 |
| Monomer composition (g) | BMPS-1 (Synthesis Example 1) | 49.35 | | 44.93 | | | |
| | BMPS-2 (Synthesis Example 2) | | 49.35 | | 44.93 | | |
| | BMPS-3 (Comparative Synthesis Example 1) | | | | | 49.35 | 44.93 |
| | PETMP | | | 3.01 | 3.01 | | 3.01 |
| | XDI | 50.65 | 50.65 | | | 50.65 | |
| | IPDI | | | 43.78 | 43.78 | | 43.78 |
| | HDI | | | 8.28 | 8.28 | | 8.28 |
| Release agent (g) | Zelec UN | 0.1 | 0.1 | 0.1 | 0.1 | 0.1 | 0.1 |
| UV absorber (g) | HOPBT | 1.5 | 1.5 | 1.5 | 1.5 | 1.5 | 1.5 |
| Polymerization initiator (g) | BTC | 0.1 | 0.1 | 0.1 | 0.1 | 0.1 | 0.1 |
| Organic dyes (ppm) | HTAQ | 20 | 20 | 20 | 20 | 20 | 20 |
| | PRD | 10 | 10 | 10 | 10 | 10 | 10 |
| Lens physical properties | Refractive index (nE, 20° C.) | 1.6697 | 1.6698 | 1.5985 | 1.5987 | 1.6696 | 1.5986 |
| | Abbe number | 32 | 32 | 47 | 47 | 32 | 47 |
| | APHA | 13 | 13 | 12 | 12 | 25 | 23 |

As can be seen from the results in Table 1, the optical lenses of Examples 1-4, each of which was obtained from the optical resin composition including the polythiol compound prepared by the inventive method and the polyisocyanate compounds, were clear and transparent. In contrast, the optical lenses of Comparative Examples 1-2 were found to have inferior colors and physical properties. These results indicate that the use of the polythiol compound prepared by the inventive methods as a major component of a polymerizable composition for a urethane optical material enables the manufacture of an optical lens with excellent optical properties at reduced cost. The polythiol compound prepared by the inventive methods can be widely used to produce materials for optical lenses, including inexpensive urethane resins for optical materials.

ABBREVIATIONS

Monomers
BMPS: Bis(2-(2-mercaptoethylthio)-3-mercaptopropyl)sulfide
PETMP: Pentaerythritol-tetrakis(3-mercaptopropionate)
GST: 2,3-Bis(2-mercaptoethylthio)propane-1-thiol
XDI: Xylylene diisocyanate
IPDI: Isophorone diisocyanate
HDI: Hexamethylene diisocyanate
Release Agent
Zelec UN: Acidic phosphate compound (ZELEC UN™, Stepan)
UV Absorber
HTAQ: 1-Hydroxy-4-(p-toluidine)anthraquinone
PRD: Perinone dye
Polymerization Initiator
BTC: Dibutyltin dichloride

The invention claimed is:

1. A method for preparing a polythiol compound from epichlorohydrin as a starting material, the method comprising:
   reacting epichlorohydrin with hydrogen sulfide to obtain bis(3-chloro-2-hydroxypropyl)sulfide;
   reacting a 2-mercaptoethanol salt with the bis(3-chloro-2-hydroxypropyl)sulfide to obtain a polyol compound;
   adding hydrochloric acid and thiourea to the polyol compound, stirring the mixture under heating, cooling the reaction mixture to room temperature, and adding a basic aqueous solution to the reaction mixture to hydrolyze the reaction product; and
   washing the hydrolysis product with water at room temperature, followed by concentration under reduced pressure.

2. A method for preparing a polymerizable composition for optical materials, the method comprising the steps of:
   (a) reacting epichlorohydrin with hydrogen sulfide to obtain bis(3-chloro-2-hydroxypropyl)sulfide; reacting a 2-mercaptoethanol salt with the bis(3-chloro-2-hydroxypropyl)sulfide to obtain a polyol compound; adding hydrochloric acid and thiourea to the polyol compound, stirring the mixture under heating, cooling the reaction mixture to room temperature; adding a basic aqueous solution to the reaction mixture to hydrolyze the reaction product; and washing the hydrolysis product with water at room temperature, followed by concentration under reduced pressure to obtain a polythiol compound,
   (b) adding a polyisocyanate compound to the polythiol compound obtained in step (a).

3. The method according to claim 2, wherein the polyisocyanate compound is selected from the group consisting of isophorone diisocyanate (IPDI), dicyclohexylmethane-4,4-isocyanate ($H_{12}$MDI), 1,6-hexamethylene diisocyanate (HDI), pentamethylene diisocyanate (PDI), bis(isocyanatomethyl)cyclohexane, 1,3,5-tris(6-isocyanatohexyl)-[1,3,5]-triazinane-2,4,6-trione (HDI trimer), phenylene diisocyanate, o,m,p-xylylene diisocyanate, α,α,α',α'-tetramethylxylylene diisocyanate, tolylene diisocyanate (TDI), 3,8-bis(isocyanatomethyl) tricyclo[5,2,1,02,06]decane, 3,9-bis(isocyanatomethyl) tricyclo[5,2,1,02,06]decane, 4,8-bis(isocyanatomethyl) tricyclo[5,2,1,02,06]decane, 2,5-bis(isocyanatomethyl) bicyclo[2,2,1]heptane, 2,6-bis(isocyanatomethyl) bicyclo[2,2,1]heptane, and mixtures thereof.

4. The method according to claim 2, further comprising another polythiol compound in addition to the polythiol compound prepared by the method according to claim 2.

5. A method for preparing an optical material comprising the steps of:
- (a) reacting epichlorohydrin with hydrogen sulfide to obtain bis(3-chloro-2-hydroxypropyl)sulfide; reacting a 2-mercaptoethanol salt with the bis(3-chloro-2-hydroxypropyl)sulfide to obtain a polyol compound; adding hydrochloric acid and thiourea to the polyol compound, stirring the mixture under heating, cooling the reaction mixture to room temperature, and adding a basic aqueous solution to the reaction mixture to hydrolyze the reaction product; and washing the hydrolysis product with water at room temperature, followed by concentration under reduced pressure to obtain a polythiol compound,
- (b) adding a polyisocyanate compound to the polythiol compound obtained in step (a) to obtain a polymerizable composition for optical materials,
- (c) cast polymerizing the polymerizable composition obtained in step (b) to obtain an optical material.

6. The method according to claim 5, wherein the optical material is an optical lens.

7. A method for preparing a polythiol compound from epichlorohydrin as a starting material, the method comprising:
- reacting epichlorohydrin with hydrogen sulfide in the presence of a catalyst to obtain bis(3-chloro-2-hydroxypropyl)sulfide;
- adding an aqueous solution of sodium hydroxide to the bis(3-chloro-2-hydroxypropyl)sulfide to obtain an epoxy compound,
- adding 2-mercaptoethanol and a catalyst to the epoxy compound to obtain a polyol compound,
- adding hydrochloric acid and thiourea to the polyol compound, stirring the mixture under heating, cooling the reaction mixture to room temperature, and adding a basic aqueous solution to the reaction mixture to hydrolyze the reaction product; and
- washing the hydrolysis product with water at room temperature, followed by concentration under reduced pressure.

8. A method for preparing a polymerizable composition for optical materials, the method comprising the steps of:
- (a) reacting epichlorohydrin with hydrogen sulfide to obtain bis(3-chloro-2-hydroxypropyl)sulfide; adding an aqueous solution of sodium hydroxide to the bis(3-chloro-2-hydroxypropyl)sulfide to obtain an epoxy compound; adding 2-mercaptoethanol and a catalyst to the epoxy compound to obtain a polyol compound; adding hydrochloric acid and thiourea to the polyol compound, stirring the mixture under heating, cooling the reaction mixture to room temperature, and adding a basic aqueous solution to the reaction mixture to hydrolyze the reaction product; and washing the hydrolysis product with water at room temperature, followed by concentration under reduced pressure to obtain a polythiol compound;
- (b) adding a polyisocyanate compound to the polythiol compound obtained in step (a).

9. The method according to claim 8, wherein the polyisocyanate compound is selected from the group consisting of isophorone diisocyanate (IPDI), dicyclohexylmethane-4,4-isocyanate ($H_{12}$MDI), 1,6-hexamethylene diisocyanate (HDI), pentamethylene diisocyanate (PDI), bis(isocyanatomethyl)cyclohexane, 1,3,5-tris(6-isocyanatohexyl)-[1,3,5]-triazinane-2,4,6-trione (HDI trimer), phenylene diisocyanate, o,m,p-xylylene diisocyanate, α,α,α',α'-tetramethylxylylene diisocyanate, tolylene diisocyanate (TDI), 3,8-bis(isocyanatomethyl) tricyclo[5,2,1,02,06]decane, 3,9-bis(isocyanatomethyl) tricyclo[5,2,1,02,06]decane, 4,8-bis(isocyanatomethyl) tricyclo[5,2,1,02,06]decane, 2,5-bis(isocyanatomethyl) bicyclo[2,2,1]heptane, 2,6-bis(isocyanatomethyl) bicyclo[2,2,1]heptane, and mixtures thereof.

10. The method according to claim 8, further comprising another polythiol compound in addition to the polythiol compound prepared by the method according to claim 8.

11. A method for preparing an optical material, the method comprising the steps of:
- (a) reacting epichlorohydrin with hydrogen sulfide to obtain bis(3-chloro-2-hydroxypropyl)sulfide; adding an aqueous solution of sodium hydroxide to the bis(3-chloro-2-hydroxypropyl)sulfide to obtain an epoxy compound; adding 2-mercaptoethanol and a catalyst to the epoxy compound to obtain a polyol compound; adding hydrochloric acid and thiourea to the polyol compound, stirring the mixture under heating, cooling the reaction mixture to room temperature, and adding a basic aqueous solution to the reaction mixture to hydrolyze the reaction product; and washing the hydrolysis product with water at room temperature, followed by concentration under reduced pressure to obtain a polythiol compound;
- (b) adding a polyisocyanate compound to the polythiol compound obtained in step (a);
- (c) cast polymerizing the polymerizable composition obtained in step (b) to obtain an optical material.

12. The method according to claim 11, wherein the optical material is an optical lens.

* * * * *